United States Patent [19]

Carling et al.

[11] Patent Number: 5,252,584
[45] Date of Patent: Oct. 12, 1993

[54] HYDROXYQUINOLONE DERIVATIVES

[75] Inventors: William R. Carling, Bishops Stortford; Paul D. Leeson, Cambridge; Kevin W. Moore, Buntingford, all of England

[73] Assignee: Merck Sharp & Dohme Limited, Hoddesdon, England

[21] Appl. No.: 801,998

[22] Filed: Dec. 3, 1991

[30] Foreign Application Priority Data

Dec. 5, 1990 [GB] United Kingdom ............... 9026389

[51] Int. Cl.$^5$ ............................................. C07D 215/56
[52] U.S. Cl. ..................................... 514/312; 546/155
[58] Field of Search ........................ 514/312; 546/155

[56] References Cited

U.S. PATENT DOCUMENTS

| | | | |
|---|---|---|---|
| 3,574,216 | 4/1971 | Bell | 546/155 |
| 4,119,720 | 10/1978 | Hardtmann | 546/155 |
| 4,362,876 | 12/1982 | Vacek | 546/155 |
| 4,659,718 | 4/1980 | Davies | 514/312 |
| 4,735,948 | 5/1988 | Wright | 514/312 |
| 4,902,693 | 2/1990 | Blythin | 514/312 |
| 4,959,363 | 9/1990 | Wentland | 546/155 |
| 5,104,884 | 4/1992 | Koródi | 514/312 |
| 5,175,151 | 12/1992 | Afonso | 546/155 |

FOREIGN PATENT DOCUMENTS

| | | | |
|---|---|---|---|
| 0303387 | 2/1989 | European Pat. Off. . | |
| 0432994 | 6/1991 | European Pat. Off. . | |
| 0269382 | 6/1989 | German Democratic Rep. | 546/155 |
| 50-159483 | 12/1975 | Japan | 546/155 |

OTHER PUBLICATIONS

Neuroscience Lett., 1991, 121, 263, Dickenson and Aydar.
Pain, 1991, 44, 179, Murray, et al.
Pain, 1991, 44, 293, Woolf and Thompson.
Eur. J. Pharmacol., 1990, 185, 1, Trullas & Skolnick.
Eur. J. Pharmacol., 1991, 193, 283, Kehne, et al.
J. Pharmacol., Ex. Ther., 1990, 255, 40, Werling, et al.
Life Sciences, 1990, 47, pp. 1427-1435 Marrazi et al.
Nature (London), 1991, 349, 414, Turski, et al.
Br. J. Pharmacol., 1990, 101, 776, Bagetta, et al.
Society for Neuro, Absts. 1990, 16, 128.11, Lipton, et al.
Science, 1990, 250, 1276, van den Pol, et al.
Proc. Natl. Acad. Sci. USA, 1986, 83, 7104-8, Wong, et al.
Proceedings of the British Pharmaco. Soc., Jul. 1991, Abs. C78, Grimwood.
Endocrinology, 1990, 127, 2223-8, Urbanski.
Christie et al. J. Neurochem. 1985, 45, 477-82.
Rudolph et al. Neurochem. Int., 1983, 5, 479-86.
Arnt Life Sciences, 1981, 28, 1597.
Walser et al J. Heterocycl. Chem., 1975, 12, 351.

*Primary Examiner*—Donald G. Daus
*Attorney, Agent, or Firm*—Robert J. North; Joseph F. DiPrima

[57] ABSTRACT

A class of 4-hydroxy-2(1H)-quinolone derivatives, substituted at the 3-position by an N-linked heteroaromatic ring system, are selective non-competitive antagonists of NMDA receptors and/or are antagonists of AMPA receptors, and are therefore of utility in the treatment of conditions, such as neurodegenerative disorders, convulsions or schizophrenia, which require the administration of an NMDA and or AMPA receptor antagonist.

3 Claims, No Drawings

HYDROXYQUINOLONE DERIVATIVES

This invention relates to a class of 4-hydroxy-2(1H)-quinolones which are substituted in the 3-position by an optionally substituted heteroaromatic ring system. These compounds are selective non-competitive antagonists of N-methyl-D-aspartate (NMDA) receptors. More particularly, the class of compounds provided by the present invention are ligands for the strychnine-insensitive glycine modulatory site of the NMDA receptor and are therefore useful in the treatment and/or prevention of neurodegenerative disorders arising as a consequence of such pathological conditions as stroke, hypoglycemia, cerebral palsy, transient cerebral ischaemic attack, cerebral ischaemia during cardiac pulmonary surgery or cardiac arrest, perinatal asphyxia, epilepsy, Huntington's chorea, Alzheimer's disease, Amyotrophic Lateral Sclerosis, Parkinson's disease, Olivo-ponto-cerebellar atrophy, anoxia such as from drowning, spinal cord and head injury, and poisoning by exogenous and endogenous NMDA receptor agonists and neurotoxins, including environmental neurotoxins.

By virtue of their NMDA receptor antagonist properties, the compounds according to the present invention are also useful as anticonvulsant and antiemetic agents, as well as being of value in the prevention or reduction of dependence on dependence-inducing agents such as narcotics.

NMDA receptor antagonists have recently been shown to possess analgesic (see, for example, Dickenson and Aydar, Neuroscience Lett., 1991, 121, 263; Murray et al., Pain, 1991, 44, 179; and Woolf and Thompson, Pain, 1991, 44, 293), antidepressant (see, for example, Trullas and Skolnick, Eur. J. Pharmacol., 1990, 185, 1) and anxiolytic (see, for example, Kehne et al., Eur. J. Pharmacol., 1991, 193, 283) effects, and the compounds of the present invention may accordingly be useful in the management of pain, depression and anxiety.

The association of NMDA receptor antagonists with regulation of the nigrostriatal dopaminergic system has recently been reported (see, for example, Werling et al., J. Pharmacol. Exp. Ther., 1990, 255, 40; Graham et al., Life Sciences, 1990, 47, PL-41; and Turski et al., Nature (London), 1991, 349, 414). This suggests that the compounds of the present invention may thus be of assistance in the prevention and/or treatment of disorders of the dopaminergic system such as schizophrenia and Parkinson's disease.

It has also been reported recently (see Lauritzen et al., Journal of Cerebral Blood Flow and Metabolism, 1991, vol. 11, suppl. 2, Abstract XV-4) that NMDA receptor antagonists block cortical spreading depression (CSD), which may thus be of clinical importance since CSD is a possible mechanism of migraine. The class of substituted 2-amino-4-phosphonomethylalk-3-ene carboxylic acids and esters described in EP-A0420806, which are stated to be selective NMDA antagonists, are alleged thereby to be of potential utility in the treatment of inter alia migraine.

Excitatory amino acid receptor antagonists, including inter alia antagonists of NMDA receptors, are alleged in EP-A-0432994 to be of use in suppressing emesis.

Recent reports in the literature have also suggested a link between the neurotoxicity of certain viruses and the deleterious effects of these viruses on an organism caused by the potentiation of neurotransmission via excitatory amino acid receptors. By virtue of their activity as antagonists of NMDA receptors, therefore, the compounds of the present invention may be effective in controlling the manifestations of neuroviral diseases such as measles, rabies, tetanus (cf. Bagetta et al., Br. J. Pharmacol., 1990, 101, 776) and AIDS (cf. Lipton et al., Society for Neuroscience Abstracts, 1990, 16, 128.11).

NMDA antagonists have, moreover, been shown to have an effect on the neuroendocrine system (see, for example, van den Pol et al., Science, 1990, 250, 1276; and Urbanski, Endocrinology, 1990, 127, 2223), and the compounds of this invention may therefore also be effective in the control of seasonal breeding in mammals.

In addition, certain compounds of the invention are antagonists of 2-amino-3-hydroxy-5-methyl-4-isoxazole-propionic acid (AMPA) receptors, also known as quisqualate receptors. An excitatory amino acid projection from the prefrontal cortex to the nucleus accumbens (a particular region of the forebrain possessing dopamine-sensitive neurones) is well known to exist (see, for example, J. Neurochem., 1985, 45. 477). It is also well known that dopaminergic transmission in the striatum is modulated by glutamate (see, for example, Neurochem. Int., 1983, 5, 479), as also is the hyperactivity associated with presynaptic stimulation of the dopamine system by AMPA in the nucleus accumbens (cf. Life Sci., 1981, 28, 1597). Compounds which are antagonists of AMPA receptors are therefore of value as neuroleptic agents.

A class of 4-hydroxy-2(1H)-quinolone derivatives, substituted at the 3-position by an optionally substituted benzotriazole ring system, is described in JP-A-50-159483. These compounds are stated to have u.v -absorbing properties and thus to be useful as u.v. light stabilizers in the production of such things as cosmetics, fibres, foods and drugs. No therapeutic utility is disclosed for the compounds described in this publication. In particular, there is no suggestion that the compounds described therein would be of assistance in solving the problem of providing an effective agent for the treatment and/or prevention of conditions requiring the administration of an antagonist of NMDA and/or AMPA receptors.

The present invention accordingly provides a pharmaceutical composition comprising a compound of formula I or a pharmaceutically acceptable salt thereof or a prodrug thereof:

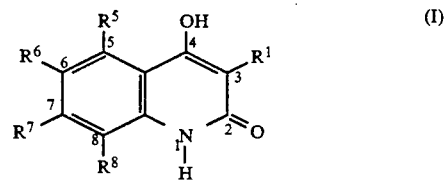

wherein
R¹ represents a group of formula (i), (ii) or (iii):

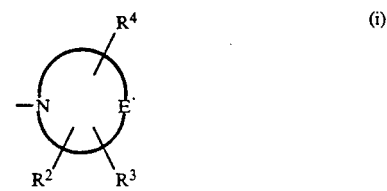

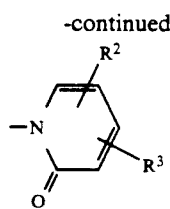

(ii)

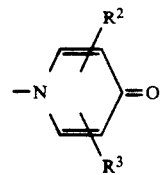

(iii)

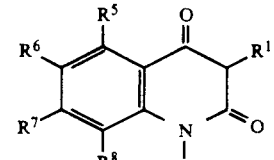

(A)

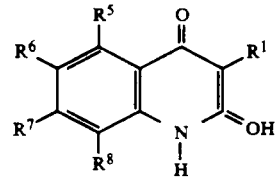

(B)

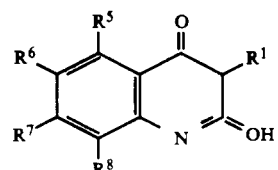

(C)

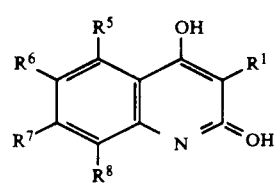

(D)

in which E represents the residue of a five-membered heteroaromatic ring containing zero, 1, 2 or 3 further nitrogen atoms;

$R^2$ and $R^3$ independently represent hydrogen, hydrocarbon, a heterocyclic group, halogen, cyano, trifluoromethyl, nitro, $-OR^a$, $-OCF_3$, $-SR^a$, $-SCF_3$, $-SOR^a$, $-SOCF_3$, $-SO_2R^a$, $-SO_2CF_3$, $-SO_2NR^aR^b$, $-NR^aR^b$, $-NR^aCOR^b$, $-NR^aCO_2R^b$, $-COR^a$, $-CO_2R^a$ or $-CONR^aR^b$ or, where appropriate, a nonbonded electron pair; or $R^2$ and $R^3$, when situated on adjacent atoms, together represent the residue of a carbocyclic or heterocyclic ring; and $R^4$ represents hydrogen, hydrocarbon, a heterocyclic group, halogen, cyano, trifluoromethyl, nitro, $-OR^a$, $-OCF_3$, $-SR^a$, $-SCF_3$, $-SOR^a$, $-SOCF_3$, $-SO_2R^a$, $-SO_2CF_3$, $-SO_2NR^aR^b$, $-NR^aR^b$, $-NR^aCOR^b$, $-NR^aCO_2R^b$, $-COR^a$, $-CO_2R^a$ or $-CONR^aR^b$;

$R^5$, $R^6$, $R^7$ and $R^8$ independently represent hydrogen, hydrocarbon, a heterocyclic group, halogen, cyano, trifluoromethyl, nitro, $-OR^a$, $-OCF_3$, $-SR^a$, $-SCF_3$, $-SOR^a$, $-SOCF_3$, $-SO_2R^a$, $-SO_2CF_3$, $-SO_2NR^aR^b$, $-NR^aR^b$, $-NR^aCOR^b$, $-NR^aCO_2R^b$, $-COR^a$, $-CO_2R^a$ or $-CONR^aR^b$; and $R^a$ and $R^b$ independently represent hydrogen, hydrocarbon or a heterocyclic group; in association with one or more pharmaceutically acceptable carriers and/or excipients.

The invention also provides a compound of formula I as defined above or a pharmaceutically acceptable salt thereof or a prodrug thereof for use in therapy.

In a further aspect, the present invention provides the use of a compound of formula I as defined above or a pharmaceutically acceptable salt thereof or a prodrug thereof for the manufacture of a medicament for the treatment and/or prevention of conditions, in particular neurodegenerative disorders, which require the administration of a selective non-competitive antagonist of NMDA receptors.

The present invention further provides the use of a compound of formula I as defined above or a pharmaceutically acceptable salt thereof or a prodrug thereof for the manufacture of a medicament for the treatment and/or prevention of conditions, such as schizophrenia, which require the administration of an antagonist of AMPA receptors.

The compound of formula I will in general exist in equilibrium with its other tautomeric forms, including those structures of formulae A to D:

wherein $R^1$ and $R^5$ to $R^8$ are as defined with reference to formula I above. Indeed, in the prior art reference cited above, the compounds disclosed therein are designated by reference to tautomeric form (D) above. It is to be understood that all tautomeric forms of the compounds of formula I, as well as all possible mixtures thereof, are included within the scope of the present invention.

The term "hydrocarbon" as used herein includes straight-chained, branched and cyclic groups containing up to 18 carbon atoms, suitably up to 15 carbon atoms, and conveniently up to 12 carbon atoms. Suitable hydrocarbon groups include $C_{1-6}$ alkyl, $C_{2-6}$ alkenyl, $C_{2-6}$ alkynyl, $C_{3-7}$ cycloalkyl, $C_{3-7}$ cycloalkyl($C_{1-6}$)alkyl, aryl and aryl($C_{1-6}$)alkyl.

The expression "a heterocyclic group" as used herein includes groups containing up to 18 carbon atoms and at least one heteroatom preferably selected from oxygen, nitrogen and sulphur. The heterocyclic group suitably contains up to 15 carbon atoms and conveniently up to 12 carbon atoms, and is preferably linked through carbon. Examples of suitable heterocyclic groups include $C_{3-7}$ heterocycloalkyl, $C_{3-7}$ heterocycloalkyl($C_{1-6}$)alkyl, heteroaryl and heteroaryl($C_{1-6}$)alkyl.

Suitable alkyl groups include straight-chained and branched alkyl groups containing from 1 to 6 carbon atoms. Typical examples include methyl and ethyl groups, and straight-chained or branched propyl and butyl groups. Particular alkyl groups are methyl, ethyl and t-butyl.

Suitable alkenyl groups include straight-chained and branched alkenyl groups containing from 2 to 6 carbon atoms. Typical examples include vinyl and allyl groups.

Suitable alkynyl groups include straight-chained and branched alkynyl groups containing from 2 to 6 carbon atoms. Typical examples include ethynyl and propargyl groups.

Suitable cycloalkyl groups include groups containing from 3 to 7 carbon atoms. Particular cycloalkyl groups are cyclopropyl and cyclohexyl.

Suitable aryl groups include phenyl and naphthyl groups.

A particular aryl($C_{1-6}$)alkyl group is benzyl.

Suitable heterocycloalkyl groups include piperidyl, piperazinyl and morpholinyl groups.

Suitable heteroaryl groups include pyridyl, quinolyl, isoquinolyl, pyridazinyl, pyrimidinyl, pyrazinyl, pyrrolyl, indolyl, pyranyl, furyl, benzofuryl, thienyl, benzthienyl, imidazolyl, oxadiazolyl and thiadiazolyl groups. Particular heteroaryl groups are pyridyl and oxadiazolyl.

The five-membered heteroaromatic ring of which E is the residue may be, for example, a pyrrole, pyrazole, imidazole, triazole or tetrazole ring, preferably a pyrrole ring.

Where $R^2$ and $R^3$ together represent the residue of a carbocyclic or heterocyclic ring, the ring may be saturated or unsaturated. The ring may suitably be a 4- to 9-membered ring, but will preferably be a 5- or 6-membered ring. Where $R^2$ and $R^3$ together represent the residue of a heterocyclic ring, this ring may contain up to four heteroatoms selected from oxygen, nitrogen and sulphur. Where the heteroatom is nitrogen it may, where appropriate, be shared with the heteroaromatic ring of which E is the residue. Suitable carbocyclic rings completed by $R^2$ and $R^3$ include cyclohexane, cyclohexene, cyclohexadiene and benzene rings. Suitable heterocyclic rings completed by $R^2$ and $R^3$ include pyridine, pyrrole, furan, thiophene, thiazole and thiadiazole rings. Alternatively, $R^2$ and $R^3$ may suitably together represent a methylenedioxy or ethylenedioxy group.

The hydrocarbon and heterocyclic groups, as well as the carbocyclic or heterocyclic ring completed by $R^2$ and $R^3$, may in turn be optionally substituted by one or more groups selected from $C_{1-6}$ alkyl, adamantyl, phenyl, halogen, $C_{1-6}$ haloalkyl, trifluoromethyl, hydroxy, $C_{1-6}$ alkoxy, aryloxy, keto, $C_{1-3}$ alkylenedioxy, nitro, cyano, carboxy, $C_{2-6}$ alkoxycarbonyl, $C_{2-6}$ alkoxycarbonyl($C_{1-6}$)alkyl, $C_{2-6}$ alkylcarbonyloxy, arylcarbonyloxy, $C_{2-6}$ alkylcarbonyl, arylcarbonyl, $C_{1-6}$ alkylthio, $C_{1-6}$ alkylsulphinyl, $C_{1-6}$ alkylsulphonyl, amino, mono- or di($C_{1-6}$)alkylamino, $C_{2-6}$ alkylcarbonylamino and $C_{2-6}$ alkoxycarbonylamino.

The term "halogen" as used herein includes fluorine, chlorine, bromine and iodine, especially chlorine.

Particular values for the substituents $R^2$ and $R^3$ include hydrogen, halogen, cyano, trifluoromethyl, nitro, hydroxy, amino, di($C_{1-6}$)alkylamino, carboxy, $C_{1-6}$ alkyl, $C_{2-6}$ alkenyl, $C_{2-6}$ alkynyl, aryl, aryl($C_{1-6}$)alkyl, phenyl($C_{2-6}$)-alkynyl, $C_{1-6}$ alkoxy, aryloxy, aryl($C_{1-6}$)alkoxy, $C_{1-6}$ alkylthio and $C_{2-7}$ alkoxycarbonyl. Suitably, one of $R^2$ and $R^3$ represents hydrogen and the other represents hydrogen, halogen, trifluoromethyl, nitro, dimethylamino, $C_{1-6}$ alkyl, phenyl, phenyl($C_{2-6}$)alkynyl, $C_{1-6}$ alkoxy, phenoxy or phenyl($C_{1-6}$)alkoxy. Alternatively, when the five-membered ring of which E is the residue is a triazole or tetrazole ring, one or both of $R^2$ and $R^3$ is a non-bonded electron pair. Preferably, at least one of $R^2$ and $R^3$ is other than hydrogen.

Where $R^2$ and $R^3$ together represent the residue of a carbocyclic or heterocyclic ring, this may be, in particular, an optionally substituted benzene ring.

The substituent $R^4$ may be, for example, hydrogen, $C_{1-6}$ alkyl or aryl. Preferably, $R^4$ is hydrogen, methyl or phenyl.

The benzo moiety of the hydroxyquinolone ring system shown in formula I above may be substituted or unsubstituted. Particular substituents include halogen, cyano, trifluoromethyl, trifluoromethoxy, trifluoromethylthio, trifluoromethylsulphonyl, nitro, hydroxy, amino, carboxy, $C_{1-6}$ alkyl, $C_{2-6}$ alkenyl, $C_{1-6}$ alkoxy, $C_{1-6}$ alkylthio and $C_{2-7}$ alkoxycarbonyl. Suitably $R^8$ is hydrogen and $R^5$, $R^6$ and $R^7$ independently represent hydrogen, halogen, cyano, trifluoromethyl, trifluoromethoxy, trifluoromethylthio, trifluoromethylsulphonyl, nitro, $C_{1-6}$ alkyl or $C_{2-6}$ alkenyl, at least one of $R^5$, $R^6$ and $R^7$ desirably being other than hydrogen Preferably, $R^6$ and $R^8$ each represents hydrogen and $R^5$ and $R^7$ independently represent hydrogen, cyano, trifluoromethyl, nitro, methyl, ethyl, vinyl or halogen, especially chlorine or iodine. In a particular embodiment, $R^7$ represents cyano, trifluoromethyl, nitro or halogen, especially chlorine; and $R^5$ is hydrogen or ethyl.

Certain compounds falling within the definition of formula I above are novel. Accordingly, in a further aspect, the invention provides a compound of formula IA or a salt or prodrug thereof:

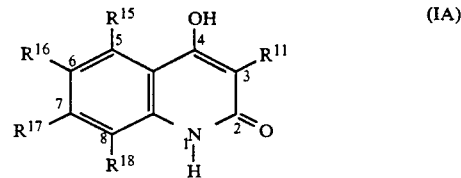

wherein
$R^{11}$ represents a group of formula (iv), (v) or (vi):

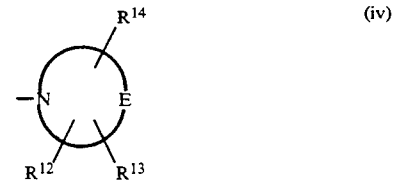

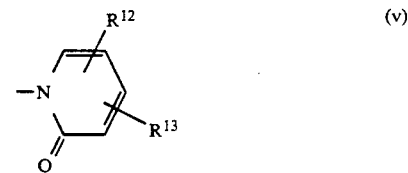

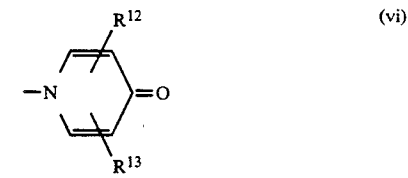

in which $E^1$ represents the residue of a five-membered heteroaromatic ring containing zero, 1, 2 or 3 further nitrogen atoms;

$R^{12}$ and $R^{13}$ independently represent hydrogen, hydrocarbon, a heterocyclic group, halogen, cyano, trifluoromethyl, nitro, $-OR^a$, $-OCF_3$, $-SR^a$, $-SCF_3$, $-SOR^a$, $-SOCF_3$, $-SO_2R^a$, $-SO_2CF_3$, $-SO_2N$-

$R^aR^b$, —$NR^aR^b$, —$NR^aCOR^b$, —$NR^aCO_2R^b$, —$COR^a$, —$CO_2R^a$ or —$CONR^aR^b$ or, where appropriate, a non-bonded electron pair; or $R^{12}$ and $R^{13}$, when situated on adjacent atoms, together represent the residue of a carbocyclic or heterocyclic ring; and $R^{14}$ represents hydrogen, hydrocarbon, a heterocyclic group, halogen, cyano, trifluoromethyl, nitro, —$OR^a$, —$OCF_3$, —$SR^a$, —$SCF_3$, —$SOR^a$, —$SOCF_3$, —$SO_2R^a$, —$SO_2CF_3$, —$SO_2NR^aR^b$, —$NP^aR^b$, —$NR^aCOR^b$, —$NR^aCO_2R^b$, —$COR^a$, —$CO_2R^a$ or —$CONR^aR^b$;

$R^{15}$, $R^{16}$, $R^{17}$ and $R^{18}$ independently represent hydrogen, hydrocarbon, a heterocyclic group, halogen, cyano, trifluoromethyl, nitro, —$OR^a$, —$OCF_3$, —$SR^a$, —$SCF_3$, —$SOR^a$, —$SOCF_3$, —$SO_2R^a$, —$SO_2CF_3$, —$SO_2NR^aR^b$, —$NR^aR^b$, —$NR^aCOR^b$, —$NR^aCO_2R^b$, —$COR^a$, —$CO_2P^a$ or —$CONR^aR^b$; and $R^a$ and $R^b$ independently represent hydrogen, hydrocarbon or a heterocyclic group; provided that, when $R^{11}$ is a group of formula (iv), then this group is not a 1,2,3-benzotriazol-2-yl ring system optionally substituted by lower alkyl, lower alkoxy or halogen.

Subject to the above proviso, the substituents $R^{11}$ to $R^{18}$ and $E^1$ in the compounds of formula IA correspond to the substituents $R^1$ to $R^8$ and E respectively as defined with reference to the compounds of formula I.

For use in medicine, the salts of the compounds of formula IA will be non-toxic pharmaceutically acceptable salts. Other salts may, however, be useful in the preparation of the compounds according to the invention or of their non-toxic pharmaceutically acceptable salts.

Suitable pharmaceutically acceptable salts of the compounds of formulae I and IA above include alkali metal salts, e.g. lithium, sodium or potassium salts; alkaline earth metal salts, e.g. calcium or magnesium salts; and salts formed with suitable organic ligands, e.g. quaternary ammonium salts. Where appropriate, acid addition salts may, for example, be formed by mixing a solution of the compound according to the invention with a solution of a pharmaceutically acceptable non-toxic acid such as hydrochloric acid, fumaric acid, maleic acid, succinic acid, acetic acid, citric acid, tartaric acid, carbonic acid or phosphoric acid.

The present invention includes within its scope prodrugs of the compounds of formulae I and IA above. In general, such prodrugs will be functional derivatives of the compounds of formulae I and IA which are readily convertible in vivo into the required compound. Conventional procedures for the selection and preparation of suitable prodrug derivatives are described, for example, in "Design of Prodrugs", ed. H. Bundgaard, Elsevier, 1985.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof are encompassed within the scope of the present invention.

One sub-class of compounds according to the invention is represented by the compounds of formula IIA and salts and prodrugs thereof:

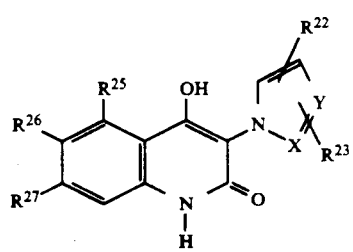

(IIA)

wherein

X and Y independently represent carbon or nitrogen;

$R^{22}$ and $R^{23}$ independently represent hydrogen, halogen, cyano, trifluoromethyl, nitro, hydroxy, amino, di($C_{1-6}$)alkylamino, carboxy, $C_{1-6}$ alkyl, $C_{2-6}$ alkenyl, $C_{2-6}$ alkynyl, aryl, aryl($C_{1-6}$)alkyl, phenyl($C_{2-6}$)alkynyl, $C_{1-6}$ alkoxy, aryloxy, aryl($C_{1-6}$)alkoxy, $C_{1-6}$ alkylthio or $C_{2-7}$ alkoxycarbonyl; and $R^{25}$, $R^{26}$ and $R^{27}$ independently represent hydrogen, halogen., cyano, trifluoromethyl, nitro, hydroxy, amino, carboxy, $C_{1-6}$ alkyl, $C_{2-6}$ alkenyl, $C_{1-6}$ alkoxy, $C_{1-6}$ alkylthio or $C_{2-7}$ alkoxycarbonyl.

Suitably, $R^{22}$ and $R^{23}$ independently represent hydrogen, $C_{1-6}$ alkyl or aryl. Particular values of $R^{22}$ and $R^{23}$ include hydrogen, methyl and phenyl. Preferably, one of $R^{22}$ and $R^{23}$ represents hydrogen, and the other represents hydrogen, methyl or phenyl.

Suitably, $R^{25}$ represents hydrogen, nitro, methyl, ethyl, vinyl or halogen, especially chlorine or iodine. Preferably, $R^{25}$ is hydrogen, ethyl or iodine.

Suitably, $R^{26}$ represents hydrogen or chlorine, preferably hydrogen.

Suitably, $R^{27}$ represents hydrogen, cyano, trifluoromethyl, nitro or halogen, preferably chlorine.

Another sub-class of compounds according to the invention is represented by the compounds of formula IIB and salts and prodrugs thereof:

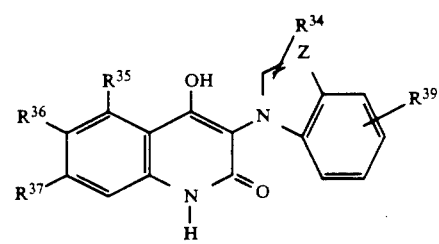

(IIB)

wherein

Z represents carbon or nitrogen;

$R^{34}$ and $R^{39}$ independently represent hydrogen, halogen, cyano, trifluoromethyl, nitro, hydroxy, amino, di($C_{1-6}$)alkylamino, carboxy, $C_{1-6}$ alkyl, $C_{2-6}$ alkenyl, $C_{2-6}$ alkynyl, aryl, aryl($C_{1-6}$)alkyl, phenyl($C_{2-6}$)alkynyl, $C_{1-6}$ alkoxy, aryloxy, aryl($C_{1-6}$)alkoxy, $C_{1-6}$ alkylthio or $C_{2-7}$ alkoxycarbonyl; and $R^{35}$, $R^{36}$ and $R^{37}$ independently represent hydrogen, halogen, cyano, trifluoromethyl, nitro, hydroxy, amino, carboxy, $C_{1-6}$ alkyl, $C_{2-6}$ alkenyl, $C_{1-6}$ alkylthio or $C_{2-7}$ alkoxycarbonyl.

Preferably, Z represents carbon.

Suitably, $R^{34}$ and $R^{39}$ independently represent hydrogen, $C_{1-6}$ alkyl, aryl or $C_{1-6}$ alkoxy. Particular values of $R^{34}$ and $R^{39}$ include hydrogen, methyl, phenyl and methoxy. Preferably, one of $R^{34}$ and $R^{39}$ represents hydrogen and the other represents hydrogen, methyl or phenyl.

Suitably, $R^{35}$ and $R^{36}$ independently represent hydrogen, nitro, methyl, ethyl, vinyl or halogen, especially chlorine or iodine. Preferably, $R^{35}$ is hydrogen, ethyl or iodine. Preferably, $R^{36}$ is hydrogen.

Suitably, $R^{37}$ represents hydrogen, cyano, trifluoromethyl, nitro or halogen, preferably chlorine.

Specific compounds within the scope of the present invention include:

7-chloro-4-hydroxy-3-(pyrrol-1-yl)-2(1H)-quinolone;
7-chloro-4-hydroxy-3-(pyrazol-1-yl)-2(1H)-quinolone;
7-chloro-4-hydroxy-3-(3-phenylindol-1-yl)-2(1H)quinolone;
7-chloro-4-hydroxy-3-(3-phenylpyrrol-1-yl)-2(1H)quinolone;
7-chloro-4-hydroxy-3-(indol-1-yl)-2(1H)-quinolone;
7-chloro-4-hydroxy-3-(3-methylindol-1-yl)-2(1H)quinolone;
7-chloro-4-hydroxy-3-(4-methylindol-1-yl)-2(1H)quinolone;
7-chloro-4-hydroxy-3-(5-methylindol-1-yl)-2(1H)quinolone;
7-chloro-4-hydroxy-3-(5-methoxyindol-1-yl)-2(1H)quinolone;
7-chloro-3-(3,5-dimethylpyrazol-1-yl)-4-hydroxy-2(1H)quinolone;
7-chloro-4-hydroxy-3-(imidazol-1-yl)-2(1H)-quinolone;
7-chloro-4-hydroxy-3-(1,2,4-triazol-1-yl)-2(1H)quinolone;
7-chloro-4-hydroxy-3-(indazol-1-yl)-2(1H)-quinolone;
7-chloro-4-hydroxy-3-(4-oxopyridin-1-yl)-2(1H)-quinolone;
7-chloro-4-hydroxy-3-(2-oxopyridin-1-yl)-2(1H)-quinolone;
7-chloro-4-hydroxy-3-(6-methylindol-1-yl)-2(1H)quinolone;

and salts and prodrugs thereof.

The pharmaceutical compositions of this invention are preferably in unit dosage forms such as tablets, pills, capsules, powders, granules, sterile solutions or suspensions, or suppositories, for oral, intravenous, parenteral or rectal administration. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

In the treatment of neurodegeneration, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day. In a particular embodiment, the compounds may be conveniently administered by intravenous infusion.

The compounds of formula I above, including the novel compounds according to the invention, may be prepared by a process which comprises cyclising a compound of formula III:

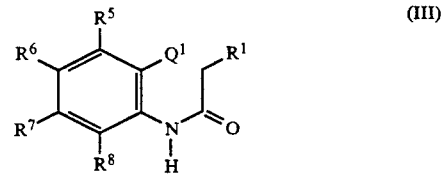

(III)

wherein $R^1$, $R^5$, $R^6$, $R^7$ and $R^8$ are as defined above; and $Q^1$ represents a reactive carboxylate moiety.

The reaction is conveniently carried out in the presence of a base, followed by a mild acidic work-up, as described, for example, in J. Heterocycl. Chem., 1975, 12, 351. Suitable bases of use in the reaction include sodium hydride and potassium hexamethyldisilazide.

Suitable values for the reactive carboxylate moiety $Q^1$ include esters, for example $C_{1-4}$ alkyl esters; acid anhydrides, for example mixed anhydrides with $C_{1-4}$ alkanoic acids; acid halides, for example acid chlorides; orthoesters; and primary, secondary and tertiary amides.

Preferably, the group $Q^1$ represents methoxycarbonyl or ethoxycarbonyl.

The intermediates of formula III above may conveniently be prepared by reacting a compound of formula $Q^2.CH_2.R^1$ with a compound of formula IV:

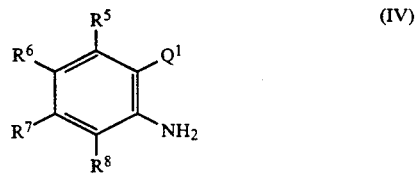

(IV)

wherein $R^1$, $R^5$, $R^6$, $R^7$, $R^8$ and $Q^1$ are as defined above; and $Q^2$ represents a reactive carboxylate moiety.

The reaction is conveniently effected by mixing the reagents in an inert solvent, such as dichloromethane or 1,2-dichloroethane, and heating the reaction mixture at an elevated temperature, for example the reflux temperature of the solvent employed.

Suitable values for the reactive carboxylate moiety $Q^2$ correspond to those defined above for Q1. Preferably, the group $Q^2$ is an acid halide group, in particular an acid chloride group. A compound of formula $Q^2.CH_2.R^1$ wherein $Q^2$ represents an acid chloride group may be prepared from the corresponding compound of formula $Q^2.CH_2.R^1$ wherein $Q^2$ represents a carboxy group $-CO_2H$ by treatment with oxalyl chloride or bis(2-oxo-3-oxazolidinyl)phosphinic chloride (BOP-Cl) under standard conditions well known from the art.

Alternatively, where the heteroaromatic moiety R1 is basic, for example where R1 represents a 1,2,4-triazolyl ring system, the intermediate of formula III may be prepared by reacting a compound of formula $R^1$-H with a compound of formula V:

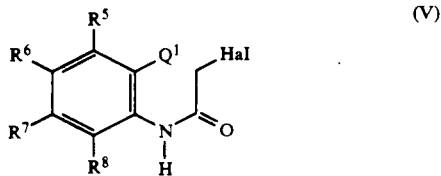

(V)

wherein $R^1$, $R^5$, $R^6$, $R^7$ and $R^8$ are defined above; and Hal represents a halogen atom, e.g. iodine.

The reaction is conveniently effected, for example, by treating the halide of formula V with the sodium salt of the heterocycle $R^1$-H in a polar solvent such as N,N-dimethylformamide at room temperature.

In an alternative process, the compounds of formula I above, including the novel compounds according to the invention, may be prepared in a single step from the intermediates of formulae IV and $Q^2.CH_2.R^1$ as defined above by treating a mixture of these reagents with approximately two equivalents of a strong base such as potassium hexamethyldisilazide.

In a further process, the compounds of formula I above, including the novel compounds according to the invention, may be prepared by cyclisation of a compound of formula VI:

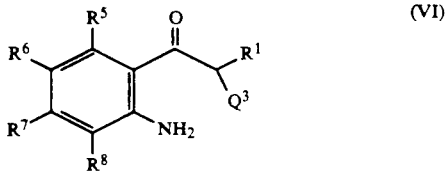

(VI)

wherein $R^1$, $R^5$, $R^6$, $R^7$ and $R^8$ are as defined above; and $Q^3$ represents a reactive carboxylate moiety.

The reaction is conveniently effected in the presence of a base such as potassium hexamethyl-disilazide.

Suitable values for the reactive carboxylate moiety $Q^3$ correspond to those defined above for $Q^1$. Preferably, the group $Q^3$ represents a $C_{1-4}$ alkyl ester group such as methoxycarbonyl or ethoxycarbonyl.

Where $Q^3$ represents a $C_{1-4}$ alkyl ester group, the intermediates of formula VI may conveniently be prepared by Claisen ester condensation of a compound of formula IV with a compound of formula $Q^3.CH_2.R^1$, wherein $Q^1$ and $Q^3$ both represent $C_{1-4}$ alkyl ester groups. This involves treating a mixture of the reactants with a strong base such as potassium hexamethyldisilazide. Under these conditions, the reactants will usually be converted in situ directly into the desired cyclised product of formula I without the necessity for isolation of the intermediate of formula VI.

The intermediates of formulae $Q^2$ $CH_2.R^1$, $Q^3.CH_2.R^1$, IV and V above, including the precursors of formula $Q^2.CH_2.R^1$ wherein $Q^2$ represents $-CO_2H$, where they are not commercially available, may be prepared by the methods described in the accompanying Examples, or by methods analogous thereto which will be readily apparent to those skilled in the art.

It will be appreciated that any compound of formula I or IA initially obtained from any of the above processes may, where appropriate, subsequently be elaborated into a further desired compound of formula I or IA respectively using techniques known from the art.

Where the above-described processes for the preparation of the compounds according to the invention give rise to mixtures of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene, *Protective Groups in Organic Synthesis*, John Wiley & Sons, 1981. The protecting groups may be removed at a convenient subsequent stage using methods known from the art.

The following Examples illustrate the preparation of compounds according to the invention.

The compounds useful in this invention potently and selectively block responses to NMDA and/or AMPA in a brain slice from rat cortex, and inhibit the binding of agonists and antagonists to the strychnine-insensitive site present on the NMDA receptor and/or AMPA binding to rat forebrain membranes.

Cortical Slice Studies

The effects of compounds of the invention on responses to NMDA and AMPA were assessed using the rat cortical slice as described by Wong et al., *Proc. Natl. Acad. Sci. USA*. 1986, 83, 7104. The apparent equilibrium constant ($K_b$) was calculated from the righthand shift in the NMDA or AMPA concentration-response curves produced by the compound under test. Of those compounds of the accompanying Examples which were tested, all were found to possess a $K_b$ value in response to NMDA of below 150 μM.

Binding Studies

The ability of test compounds to displace $^3$H-L-689,560 (trans-2-carboxy-5,7-dichloro-4-phenylaminocarbonylamino-1,2,3,4-tetrahydroquinolone) binding to the strychnine-insensitive site present on the NMDA receptor of rat forebrain membranes was determined by the method of Grimwood et al., *Proceedings of The British Pharmacological Society, July* 1991, Abstract C78. The concentration of the compounds of the accompanying Examples required to displace 50% of the specific binding (IC$_{50}$) is below 50 μM in each case.

EXAMPLE 1

7-Chloro-4-hydroxy-3-(pyrrol-1-yl)-2(1H)-quinolone

Pyrrole-1-acetic acid methyl ester (0.7 g, 0.005M) and 7-chloro anthranilic acid methyl ester (0.94 g, 1 meq) were dissolved in dry tetrahydrofuran (40 ml) and potassium hexamethyl disilazide (KHMDS) (24.15 ml of a 0.5 molar solution in toluene, 2.4 molar equivalents) added in one portion. The reaction mixture was stirred at room temperature for 3h then quenched with methanol (10 ml) and concentrated in vacuo. The residue was partitioned between sodium hydroxide solution and diethyl ether then the separated aqueous extracts were acidified to pH1 with concentrated hydrochloric acid and the solid produced was collected by filtration then recrystallized from dimethylformamide/water to give the title compound as an off-white solid (0.048 g) m.p.>280° C. dec; δ(360 MHz, DMSO) 6.15 (2H, t, J=2.1 Hz, 2' pyrrole protons); 6.76 (2H, t, J=2.1 Hz, 1' pyrrole protons), 7.26 (1H, dd, J=8.6 and 2.0 Hz, 6-H); 7.34 (1H, d, J=2.0 Hz, 8-H), 7.96 (1H, d, J=8.6 Hz, 5-H); m/e 260 (M+); Found C, 58.75; H, 3.42; N, 10.30. C$_{13}$H$_9$ClN$_2$O$_2$.0.25 H$_2$O requires C, 58.88; H, 3.61; N, 10.58%.

EXAMPLE 2

7-Chloro-4-hydroxy-3-(pyrazol-1-yl)-2(1H)-quinolone

This compound was prepared in the same way as that described in Example 1 except using pyrazole-1-acetic acid methyl ester instead of pyrrole-1-acetic acid methyl ester to give the title compound as an off-white solid (m.p. 310° C.) δ(360 MHz, DMSO) 6.59 (1H, s, 4' pyrazole proton); 7.29 (1H, dd, J=8.5 and 2.0 Hz, 6-H); 7.37 (1H, d, J=2.0 Hz, 8-H), 7.90 (1H, d, J=1.4 Hz, 3' or 5' pyrazole proton); 7.96 (1H, d, J=8 Hz, 5-H); 8.89 (1H, d, J=1.4 Hz, 3' or 5' pyrazole proton); 12.00 (1H, br, s, NH); m/e 261 (M+); Found C, 54.90; H, 2.99; N, 15.86. C$_{12}$H$_8$ClN$_3$O$_2$ requires C, 55.08; H, 3.08; N, 16.06%.

EXAMPLE 3

7-Chloro-4-hydroxy-3-(3-phenylindol-1-yl)-2(1H)quinolone

3-Phenyl indole (2 g, 0.0094 M) in dry tetrahydrofuran (100 ml) was cooled to −78∞ C. and potassium hexamethyldisilazide (18.78 ml of a 0.5 molar solution in toluene, 1 molar equivalent) was added. The reaction mixture was removed from cooling and stirred for 15 minutes then cooled again to −78° C. and methyl bromoacetate (0.98 ml, 1.1 molar equivalents) was added. The reaction solution was allowed to warm to room temperature and stirred for 14h, concentrated in vacuo and partitioned between ethyl acetate and water. The organic layer was dried (Na$_2$SO$_4$), filtered and concentrated under vacuum to leave a residue which was dissolved in dry tetrahydrofuran (100 ml) with 7-chloro anthranilic acid methyl ester (1.725 g, 0.0094M) and potassium hexamethyldisilazide (52.64 ml of a 0.5 molar solution in toluene) which was added in one portion. After stirring at room temperature for 3h, the reaction mixture was quenched with methanol (15 ml) and the solvents evaporated under vacuum. The residue was partitioned between diethyl ether and sodium hydroxide solution, the aqueous layer was acidified to pH1 with concentrated hydrochloric acid and the solid produced was collected by filtration and recrystallised from dimethylformamide/water (850 mg, m.p. 224°-226° C.) δ(360 MHz, DMSO) 7.10-7.32 (5H, m, 6-H and 4 other aromatic protons); 7.39 (1H, d, J=1.8 Hz, 8-H); 7.48 (2H, m, aromatic protons); 7.64 (1H, s, 2'-insole proton); 7.73 (2H, aromatic protons); 7.95 (1H, m, aromatic proton); 7.99 (1H, d, J=8.7 Hz, 5-H); 11.48 (1H, br, s, OH); 11.83 (1H, br, s, NH); m/e 386 (M+); Found C, 69.01; H, 4.09; N, 6.91. C$_{23}$H$_{15}$ClN$_2$O$_2$.0.75-H$_2$O requires C, 69.00; H, 4.15; N, 7.00%.

EXAMPLE 4

7-Chloro-4-hydroxy-3-(3-phenylpyrrol-1-yl)-1(1H)quinolone

This compound was prepared in the same way as that described in Example 3 except using 3-phenyl pyrrole in place of 3-phenyl indole to give the title compound as a white solid (m.p.>320° C. dec) δ(360 MHz, DMSO) 6.59 (1H, s, pyrrole proton); 6.81 (1H, s, pyrrole proton), 7.10-7.58 (8H, m, 1 pyrrole proton. 6-H, 8-H and 5 aromatic protons); 7.96 (1H, d, J=8.7 Hz, 5-H); 11.29 (1H, br, s, OH); 11.78 (1H, s, NH); m/e 336 (M+); Found C, 65.67; H, 3.76; N, 7.99. C$_{19}$H$_{13}$ClN$_2$O$_2$.0.6-H$_2$O requires C, 65.66; H, 4.12; N, 8.06%.

EXAMPLE 5

7-Chloro-4-hydroxy-3-(indol-1yl)-2(1H)quinolone

This compound was prepared in the same way as that described for Example 3 except using indole in place of 3-phenyl indole to give the title compound as a white solid (m.p. 288° C. decomp). δ(360 MHz, DMSO) 6.60 (1H, d, J=3.2 Hz, indole proton); 7.01 (1H, m, indole proton); 7.07 (2H, m, indole protons); 7.27 (2H, m, 6-H and 8-H); 7.38 (1H, d, J=1.9 Hz, indole proton); 7.60 (1H, m, indole proton); 7.98 (1H, d, J=8.6 Hz, 5-H); 11.31 (1H, br, s, OH); 11.78 (1H, s, NH); m/e 310 (M+); Found: C, 62.98; H, 3.79; N, 8.90. C$_{17}$H$_{11}$ClN$_2$O$_2$.1.5-H$_2$O requires C, 62.99; H, 8.64; N, 3.89%.

EXAMPLE 6

7-chloro-4-hydroxy-3-(3-methylindol-1-yl)-2(1H)-quinolone

This compound was prepared in the same way as that described for Example 3 except 3-methyl indole was used in place of 3-phenyl indole to give the title compound as a white solid (m.p.>290° C. decomp). δ(360 MHz, DMSO) 2.31 (3H, d, J=0.6 Hz, indole methyl); 6.93 (1H, m, indole proton); 7.03 (1H, d, J=0.9 Hz, indole proton); 7.06 (2H, m, indole protons), 7.28 (1H, dd, J=8.6 and 1.8 Hz, 6-H); 7.36 (1H, d, J=1.8 Hz, 8-H); 7.53 (1H, m, indole proton); 7.95 (1H, d, J=8.6 Hz, 5-H); 11.16 (1H, br, s, OH); 11.75 (1H, s, NH); m/e 324 (M+); Found: C, 66.03; H, 4.07; N, 8.32. C$_{18}$H$_{13}$ClN$_2$O$_2$.0.1H$_2$O requires C, 66.20; H, 4.07; N, 8.58%.

EXAMPLE 7

7-Chloro-4-hydroxy-3-(4-methylindol-1-2(1H)quinolone

This compound was prepared in the same way as that described for Example 3 except using 4-methyl indole in place of 3-phenyl indole to give the title compound as a white solid (m.p.>350° C. decomp); δ(360 MHz, DMSO) 2.52 (3H, s, indole methyl); 6.62 (1H, d, J=2.9 Hz, 3' indole proton); 6.80 (1H, d, J=8.1 Hz, 5' indole proton); 6.86 (1H, d, J=7.1 Hz, 7' indole proton); 6.97 (1H, m, 6' indole proton); 7.23 (1H, d, J=3.2 Hz, 2' indole proton); 7.28 (1H, dd, J=8.6 Hz and 1.9 Hz, 6-H); 7.37 (1H, d, J=1.8 Hz, 8-H); 7.96 (1H, d, J=8.6 Hz, 5-H), 11.25 (1H, br, s, OH); 11.75 (1H, s, NH); m/e 324 (M+).

EXAMPLE 8

7-Chloro-4-hydroxy-3-(5-methylindol-1-yl)-2(1H)quinolone

This compound was prepared in the same way as that described for Example 3 except using 5-methyl indole in place of 3-phenyl indole to give the title compound as a white solid (m.p.>350° C. dec); δ(360 MHz, DMSO) 2.39 (3H, s, indole methyl); 6.50 (1H, d, J=3.1 Hz, indole proton); 6.89 (2H, m, indole protons); 7.20 (1H, d, J=3.1 Hz, indole proton); 7.28 (1H, dd, J=8.6 Hz and 2.0 Hz, 6-H); 7.37 (1H, d, J=2.0 Hz, 8-H); 7.97 (1H, d, J=8.6 Hz, 5-H); 11.24 (1H, br, s, OH); 11.76 (1H, s, NH); m/e 324 (M+); Found: C, 66.53; H, 4.15; N, 8.41; $C_{18}H_{13}ClN_2O_2$ requires C, 66.57; H, 4.03; N, 8.63%.

EXAMPLE 9

7-Chloro-4-hydroxy-3-(5-methoxyindol-1-yl)-2(1H)quinolone

This compound was prepared in the same way as that described in example 1 using 5-methoxyindole-1-acetic acid methyl ester instead of pyrrole-1-acetic acid methyl ester to give the title compound as an off-white solid (m.p. 298° C. decomp.) δ(360 MHz, DMSO), 3.77 (3H, s, OCH₃) 6.51 (1H, d, J=3.0 Hz, indole-H), 6.73 (1H, dd, J=8.8 and 1.8 Hz, indole-6H), 6.68 (1H, d, J=8.8 Hz, indole 7-H), 7.11 (1H, d, J=1.8 Hz, indole-4H), 7.22 (1H, d, J=3.0 Hz, indole-H), 7.28 (1H, d, J=2.0 Hz, 6-H), 7.27 (1H, dd, J=8.5 and 2.0 Hz, 8-H), 7.96 (1H, d, J=8.5 Hz, 5-H), 11.25 (1H, br, s, OH), 11.76 (1H, s, NH); m/e 341 (M+1); Found C, 62.45; H, 3.59; N, 7.88; $C_{18}H_{13}ClN_2O_3 \cdot 0.2H_2O$ requires C, 62.78; H, 3.92; N, 8.13%.

EXAMPLE 10

7-Chloro-3-(3,5-dimethylpyrazol-1-yl)-4-hydroxy-2(1H)quinolone 3,5-Dimethyl pyrazole (5 g, 0.052M) was dissolved in dry THF (300 ml) under an atmosphere of nitrogen and cooled to −78° C. Potassium hexamethyldisilazide (11.4 ml of a 0.5 molar solution in toluene, 1.1 molar equivalent) was added then the reaction mixture was removed from cooling and stirred for 30 minutes, then cooled again to −30° C. and methyl bromoacetate (4.92 ml, 0.052M 1 molar equivalent) was added. The reaction solution was allowed to warm to room temperature and stirred for 17 hours, then concentrated in vacuo. 6N HCl (200 ml) was added and the reaction mixture was extracted with diethyl ether. The aqueous extracts were neutralised with solid sodium carbonate, extracted with dichloromethane and the combined organic layers were washed successively with water, saturated sodium hydrogen carbonate and saturated sodium chloride, then dried (MgSO₄) filtered and concentrated under vacuum to give a residue which was dissolved in methanol (60 ml), acetone (60 ml) and water (120 ml) with solid sodium hydroxide (1 g). After stirring at room temperature for 15 hours, the organic solvents were removed under vacuum and the aqueous layer was washed with diethyl ether and acidified to pH4 with concentrated hydrochloric acid. After extraction with ethyl acetate the organic layer was dried (MgSO₄), filtered and concentrated in vacuo. The residue was dissolved in dry dichloromethane (15 ml) under an atmosphere of nitrogen, cooled to 0° C. and oxalyl chloride (0.425 ml, 4.5 mmol 1.5 molar equivalents) and a few drops of dry N,N-dimethylformamide was added. The reaction mixture was allowed to warm to room temperature and stirred for 2 hours. then concentrated in vacuo to leave a residue which was azeotroped with toluene and evaporated under reduced pressure. The residue was dissolved in dry dichloromethane (20 ml) under a nitrogen atmosphere with 7-chloro anthranilic acid methyl ester (0.56 g, 0.003 mol 1 molar equivalent). The solution was heated to reflux for 5 hours, cooled to room temperature and concentrated in vacuo. The residue was chromatographed on SiO₂ eluting with 10% ethyl acetate/dichloromethane. The residue was dissolved in dry tetrahydrofuran (15 ml) under a nitrogen atmosphere, cooled to 0° C. and potassium hexamethyldisilazide (6.3 ml of 0.5M solution in toluene 2.4 molar equivalents) added. The reaction mixture was allowed to warm to room temperature and stirred for 2 hours, then methanol (5 ml) was added and the solvents were evaporated under vacuum. The residue was partitioned between diethyl ether and 1N sodium hydroxide solution, the aqueous layer was acidified to pH1 with concentrated hydrochloric acid and the solid produced was collected by filtration and recrystallised from dimethyl formamide/water (134 mg, m.p. 305° C.) δ(360 MHz, DMSO) 2.01 (3H, s, pyrazole methyl); 2.16 (3H, s, pyrazole methyl); 5.99 (1H, s, pyrazole proton); 7.24 (1H, dd, J=8.6 Hz and 2.0 Hz, 6-H); 7.32 (1H, d, J=2.0 Hz, 8-H); 7.91 (1H, d, J=8.6 Hz, 5-H); 11.62 (1H, s, NH); m/e 289 (M+); Found: C, 57.69; H, 4.04; N, 14.14. $C_{14}H_{12}ClN_3O_2$ requires C, 58.04; H, 4.18; N, 14.50%.

EXAMPLE 11

7-Chloro-4-hydroxy-3-(midazol-1-yl)-2-(1H) quinolone

This compound was prepared in the same way as that described in example 1 except using imidazole-1-acetic methyl ester to give the title compound as an off-white solid (m.p. 360° C. decomp.) δ(360 MHz, DMSO) 7.00 (1H, dd, J=8.4 and 1.8 Hz, 6-H), 7.17 (1H, d, J=1.75 Hz, 8-H), 7.58 (1H, s, imidazole-H), 7.75 (1H, s, imidazole-H), 7.90 (1H, d, J=8.4 Hz, 5-H), 9.12 (1H, s, imidazole-H), 10.48 (1H, s, NH), m/e 262 (M+1), Found C, 55.00; H, 3.31; N, 16.16; $C_{12}H_8ClN_3O_2$ requires C, 55.08; H, 3.08; N, 16.06.

EXAMPLE 12

7-Chloro-4-hydroxy-3-(1,2,4-triazol-1-yl)-2-(1H)-quinolone

To a solution of 7-chloro-anthranilic acid methyl ester (1 g) in dry dichloroethane (30 ml) was added chloroacetylchloride (0.42 ml). The mixture was heated to reflux for 2 hrs then cooled to room temperature and concentrated in vacuo to give a crude product (1.1 g).

To a portion of this crude product (0.65 in dry acetone was added sodium iodide (4 g) and the solution was heated under reflux for 1 hour, cooled to room temperature, filtered and concentrated in vacuo to yield a crude product. To this product was added dry dimethylformamide (15 ml) and 1,2,4-triazole sodium salt (226 mg). The mixture was stirred at room temperature for 2h then a solution of potassium hexamethyldisidazide (9.92 ml of a 0.5 molar solution in toluene) was added. The reaction mixture was stirred at room temperature for 2 hrs then quenched with methanol (5 ml) and concentrated in vacuo. The residue was partitioned between sodium hydroxide solution (1M) and diethylether, the separated aqueous extract was acidified to pH1 with concentrated hydrochloric acid and the solid produced was collected by filtration then recrystallised from dimethylformamide/water to give the title compound as an off-white solid (0.90 g, m.p. 228°-230° C. decomp.) $\delta$(360 Mhz, DMSO) 7.26 (1H, dd, J=8.6 and 2.6 Hz, 6-H), 7.37 (1H, d, J=2.6 Hz, 5-H), 7.95 (1H, d, J=8.6 Hz, 8-H), 8.12 (1H, s, triazole-H), 8.70 1H, s, triazole-H), 11.97 (1H, s, NH); m/e 263 (M+1); Found C, 50.26; H, 2.55; N, 20.48; $C_{11}H_7ClN_4O_2.0.2\ CH_3OH$ requires C, 50.00; H, 2.92; N, 20.82%.

EXAMPLE 13

7-Chloro-4-hydroxy-3-(inidazol-1-yl)-2-(1H)quinolone

This compound was prepared in the same way as that described in example 1 except using benzimidazole-1-acetic acid to give the title compound as a white solid (m.p.>410° C.), (360 MHz, NaOD, $D_2O$) $\delta$7.11 (1H, dd, J=8.7 and 2.0 Hz, 6-H), 7.26-7.40 (4H, m, 8-H and 3×benzimidazole protons), 7.80 (1H, dd, J=8.5 and 2.0 Hz, benzamidazole protons), 7.91 (1H, d, J=8.7 Hz, 5-H), 8.12 (1H, s, benzamidazole-2H).

EXAMPLE 14

7-Chloro-4-hydroxy-3-(2-oxo pyrid-1-yl)-2(1H)quinolone

This compound was prepared in same way as that described in example 1 except using 2-pyridone-1-acetic acid methyl ester to give the title compound as a white solid (m.p. 355° C. slow decomp.) $\delta$(360 MHz, DMSO) 6.23 (1H, m, pyridone-H), 6.43 (1H, d, J=9.2 Hz, pyridone-H), 7.25-7.47 (4H, m, pyridone-H×3, 6-H, 8-H), 7.92 (1H, d, J=8.6 Hz, 5-H), 11.54 (1H, br, s, OH), 11.77 (1H, s, NH), m/e 289 (M+1); Found C, 58.15; H, 32.4; N, 9.37; $C_{14}H_9ClN_2O_3$ requires C, 58.25; H, 3.14; N, 9.70.

EXAMPLE 15

7-Chloro-4-hydroxy-3-(4-oxo pyrid-1yl)-2(1H) quinolone

This compound was prepared in the same way as that described in Example 1 except using 4-pyridone-1-acetic acid methyl ester to give the title compound as a white solid (m.p. 340° C. slow decomp.) $\delta$(360 MHz, NaOD-$D_2O$) 6.70 (2H, d, J=7.5 Hz, 3 and 5 pyridone protons), 7.60 (1H, dd, J=8.7 and 2.0 Hz, 6-H), 7.35 (1H, d, J=2.0 Hz, 8-H), 7.71 (2H, d, J=7.5 Hz, 2 and 6 pyridone protons), 7.89 (1H, d, J=8.7 Hz, 5-H), m/e 289 (M+1).

EXAMPLE 16

7-Chloro-4-hydroxy-3-(6-methylindol-1yl-2(1H)-quinoline

This compound was prepared in the same way as that described for example 3 except using 5-methyl indole in place of 3-phenyl indole to give the title compound as a white solid (m.p.>350° C. decomp.); $\delta$(360 MHz, DMSO) 2.34 (3H, s, indole methyl); 6.53 (1H, d, J=3.2 Hz, indole proton); 6.79 (1H, s, indole proton); 6.89 (1H, d, J=8.0 Hz, indole proton), 7.16 (1H, d, J=3.2 Hz, indole proton), 7.28 (1H, dd, J=8.6 and 2.0 Hz, 6H), 7.38 (1H, J=1.8 Hz, 8); 7.47 (1H, d, J=8.0 Hz, indole proton), 7.98 (1H, d, J=8.6 Hz, 5H), 11.26 (1H, br, s, OH), 11.75 (1H, s, NH); m/e 324 (M+).

EXAMPLE 17

Tablet Preparation

Tablets containing 1.0, 2.0, 25.0, 26.0, 50.0 and 100.0 mg, respectively of the following compounds are prepared as illustrated below:
7-Chloro-4-hydroxy-3-(pyrrol-1-yl)-2(1H)-quinolone
7-Chloro-4-hydroxy-3-(3-phenylindol-1yl)-2(1H)-quinolone
7-Chloro-4-hydroxy-3-(3-phenylpyrrol-1-yl)1(1H)-quinolone

| TABLE FOR DOSES CONTAINING FROM 1-25 MG OF THE ACTIVE COMPOUND | | | |
|---|---|---|---|
| | Amount - mg | | |
| Active Compound | 1.0 | 2.0 | 25.0 |
| Microcrystalline cellulose | 49.25 | 48.75 | 37.25 |
| Modified food corn starch | 49.25 | 48.75 | 37.25 |
| Magnesium stearate | 0.50 | 0.50 | 0.50 |

| TABLE FOR DOSES CONTAINING FROM 26-100 MG OF THE ACTIVE COMPOUND | | | |
|---|---|---|---|
| | Amount - mg | | |
| Active Compound | 26.0 | 50.0 | 100.0 |
| Microcrystalline cellulose | 52.0 | 100.0 | 200.0 |
| Modified food corn starch | 2.21 | 4.25 | 8.5 |
| Magnesium stearate | 0.39 | 0.75 | 1.5 |

All of the active compound, cellulose, and a portion of the corn starch are mixed and granulated to 10% corn starch paste. The resulting granulation is sieved, dried and blended with the remainder of the corn starch and the magnesium stearate. The resulting granulation is then compressed into tablets containing 1.0 mg, 2.0 mg, 25.0 mg, 26.0 mg, 50.0 mg and 100 mg of the active ingredient per tablet.

What is claimed is:
1. A compound represented by formula IIA:

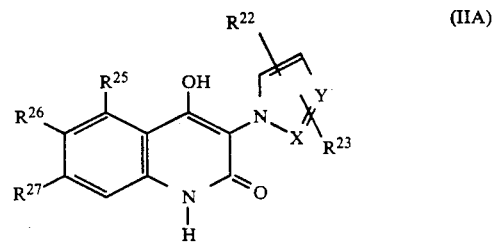

or a pharmaceutically acceptable salt thereof,
wherein
X and Y independently represent carbon or nitrogen;

$R^{22}$ and $R^{23}$ are attached to ring carbons and are independently selected from the group consisting of hydrogen, halogen, cyano, trifluoromethyl, nitro, hydroxy, amino, di($C_{1-6}$)alkylamino, carboxy, $C_{1-6}$ alkyl, $C_{2-6}$ alkenyl, $C_{2-6}$ alkynyl, phenyl, naphthyl, benzyl, phenyl ($C_{2-6}$) alkynyl, $C_{1-6}$ alkoxy, phenoxy, naphthyloxy, phenyl ($C_{1-6}$) alkoxy, naphthyl ($C_{1-6}$) alkoxy, $C_{1-6}$ alkylthio and $C_{2-7}$ alkoxycarbonyl; and $R^{25}$ represents hydrogen, nitro, methyl, ethyl, vinyl or halogen;

$R^{26}$ represents hydrogen or chlorine;

$R^{27}$ represents hydrogen, cyano, trifluoromethyl, nitro or halogen.

2. A compound of claim 1 selected from the group consisting of 7-chloro-4-hydroxy-3-(pyrrol-1-yl)-2(1H)-quinolone;

7-chloro-4-hydroxy-3-(pyrazol-1-yl)-2(1H)-quinolone;

7-chloro-4-hydroxy-3-(3phenylpyrrol-1-yl)-2-(1H)-quinolone;

7-chloro-3-(3,5-dimethylpyrazol-1-yl)-4-hydroxy-2-(1H)-quinolone;

7-chloro-4-hydroxy-3-(imidazol-1-yl)-2(1H)-quinolone; or a pharmaceutically acceptable salt thereof.

3. A pharmaceutical composition comprising an effective amount of a compound of formula IIA, or pharmaceutically acceptable salt thereof, as defined in claim 1 in association with one or more pharmaceutically acceptable carriers and/or excipients.

* * * * *